(12) United States Patent
Chanh et al.

(10) Patent No.: US 7,718,779 B2
(45) Date of Patent: May 18, 2010

(54) PROPHYLACTIC AND THERAPEUTIC MONOCLONAL ANTIBODIES

(75) Inventors: Tran C. Chanh, Lovettsville, VA (US); Gerard P. Andrews, Laramie, WY (US); Jeffrey J. Adamovicz, Thurmont, MD (US); Bradford S. Powell, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 945 days.

(21) Appl. No.: 10/987,533

(22) Filed: Nov. 12, 2004

(65) Prior Publication Data

US 2005/0220797 A1    Oct. 6, 2005

Related U.S. Application Data

(60) Provisional application No. 60/519,384, filed on Nov. 12, 2003.

(51) Int. Cl.
| | |
|---|---|
| *C12P 21/08* | (2006.01) |
| *A61K 39/40* | (2006.01) |
| *A61K 39/395* | (2006.01) |
| *C12N 5/07* | (2010.01) |
| *C12N 5/00* | (2006.01) |
| *C12P 21/04* | (2006.01) |

(52) U.S. Cl. ............... 530/388.4; 530/388.2; 530/388.1; 424/150.1; 424/141.1; 435/332; 435/326; 435/340; 435/346; 435/70.21

(58) Field of Classification Search ............... 530/388.4, 530/388.1, 388.2, 809; 424/150.1, 141.1; 435/332, 326, 340, 346, 70.21; 935/89

See application file for complete search history.

(56) References Cited

OTHER PUBLICATIONS

Glynn et al. Vaccine 23: 1957-1965, 2005.*
Leary et al. Microb. Pathogen. 23: 167-179, 1997.*
Hill et al. Infect. Immun. 71: 2234-2238, Aug. 2003.*
Hill et al. Infect. Immun. 65: 4476-4482, 1997.*
Weeks et al. Microbial Pathoegensis 32: 227-237, 2002.*
Anderson Jr. et al. Infect. Immun. 64: 4580-4585, 1996.*
Worsham et al. In: Contrib. Microbiol. Immunol. Basel, Karger, 13: 325-328, 1995.*
Davis et al. Arch. Pathol. Lab. Med. 120: 156-163, 1996.*

* cited by examiner

*Primary Examiner*—S. Devi
(74) *Attorney, Agent, or Firm*—Elizabeth Arwine (57) ABSTRACT

In this application are described monoclonal antibodies which specifically recognize V antigen of *Y. pestis* and epitopes recognized by these monoclonal antibodies. Also provided are mixtures of antibodies of the present invention, as well as methods of using individual antibodies or mixtures thereof for the detection, prevention, and/or therapeutical treatment of plague infections in vitro and in vivo.

10 Claims, 3 Drawing Sheets

Figure 1. Direct Binding of a Representative Monoclonal Anti-V Antibody to rV-Coated Microtiter Wells.

Figure 2a. Standard Binding Curve of Anti-V Antibody

Figure 2b. Standard Inhibition Curve of Anti-V Antibody

Figure 3
Illustration of IYSVIQAEINK antibody binding site

Three-D illustration of V protein structure indicating regions of beta-sheet (ribbon) and alpha helix (coil). Internal polar bonds within IYSVIQAEINK region (pink) are depicted in dots.

SEQUENCE LISTING

```
<160> NUMBER OF SEQ ID NOS: 3

<210> SEQ ID NO 1
<211> LENGTH: 326
<212> TYPE: PRT
<213> ORGANISM: Yersinia Pestis
<220> FEATURE:
<223> OTHER INFORMATION: V antigen

<400> SEQUENCE: 1

Met Ile Arg Ala Tyr Glu Gln Asn Pro Gln
 1               5                  10

His Phe Ile Glu Asp Leu Glu Lys Val Arg
                15                  20

Val Glu Gln Leu Thr Gly His Gly Ser Ser
                25                  30

Val Leu Glu Glu Leu Val Gln Leu Val Lys
                35                  40

Asp Lys Asn Ile Asp Ile Ser Ile Lys Tyr
                45                  50

Asp Pro Arg Lys Asp Ser Glu Val Phe Ala
                55                  60

Asn Arg Val Ile Thr Asp Asp Ile Glu Leu
                65                  70

Leu Lys Lys Ile Leu Ala Tyr Phe Leu Pro
                75                  80

Glu Asp Ala Ile Leu Lys Gly Gly His Tyr
                85                  90

Asp Asn Gln Leu Gln Asn Gly Ile Lys Arg
```

```
                95                 100
Val Lys Glu Phe Leu Glu Ser Ser Pro Asn
            105                 110

Thr Gln Trp Glu Leu Arg Ala Phe Met Ala
            115                 120

Val Met His Phe Ser Leu Thr Ala Asp Arg
            125                 130

Ile Asp Asp Asp Ile Leu Lys Val Ile Val
            135                 140

Asp Ser Met Asn His His Gly Asp Ala Arg
            145                 150

Ser Lys Leu Arg Glu Glu Leu Ala Glu Leu
            155                 160

Thr Ala Glu Leu Lys Ile Tyr Ser Val Ile
            165                 170

Gln Ala Glu Ile Asn Lys His Leu Ser Ser
            175                 180

Ser Gly Thr Ile Asn Ile His Asp Lys Ser
            185                 190

Ile Asn Leu Met Asp Lys Asn Leu Tyr Gly
            195                 200

Tyr Thr Asp Glu Glu Ile Phe Lys Ala Ser
            205                 210

Ala Glu Tyr Lys Ile Leu Glu Lys Met Pro
            215                 220

Gln Thr Thr Ile Gln Val Asp Gly Ser Glu
            225                 230

Lys Lys Ile Val Ser Ile Lys Asp Phe Leu
            235                 240

Gly Ser Glu Asn Lys Arg Thr Gly Ala Leu
            245                 250

Gly Asn Leu Lys Asn Ser Tyr Ser Tyr Asn
            255                 260

Lys Asp Asn Asn Glu Leu Ser His Phe Ala
            265                 270

Thr Thr Cys Ser Asp Lys Ser Arg Pro Leu
            275                 280

Asn Asp Leu Val Ser Gln Lys Thr Thr Gln
            285                 290

Leu Ser Asp Ile Thr Ser Arg Phe Asn Ser
            295                 300

Ala Ile Glu Ala Leu Asn Arg Phe Ile Gln
            305                 310

Lys Tyr Asp Ser Val Met Gln Arg Leu Leu
            315                 320

Asp Asp Thr Ser Gly Lys
            325

<210> SEQ ID NO 2
<211> LENGTH: 11
<212> TYPE: PRT
<213> ORGANISM: Yersinia Pestis
<220> FEATURE:
<223> OTHER INFORMATION: V antigen epitope
```

-continued

```
<400> SEQUENCE: 2

Ile Tyr Ser Val Ile Gln Ala Glu Ile Asn
 1               5                  10

Lys

<210> SEQ ID NO 3
<211> LENGTH: 15
<212> TYPE: PRT
<213> ORGANISM: Yersinia Pestis
<220> FEATURE:
<223> OTHER INFORMATION: V antigen epitope

<400> SEQUENCE: 3

Ala Tyr Glu Gln Asn Pro Gln His Phe Ile
 1               5                  10

Glu Asp Leu Glu Lys
                15
```

PROPHYLACTIC AND THERAPEUTIC MONOCLONAL ANTIBODIES

This application claims the benefit of priority from an earlier filed provisional application Ser. No. 60/519,384 filed on Nov. 12, 2003.

INTRODUCTION

Bubonic plague whose causative agent is the bacterium *Yersinia pestis* is a zoonotic infection that is spread from natural reservoirs via the bite of infected fleas. The bubonic form of the disease characterized by a severe inflammation of the lymph nodes involved can develop into a highly infectious pneumonic form that is spread from person to person in airborne droplets. The pneumonic form of the disease is highly contagious and is usually fatal without treatment. Due to the high infectivity and mortality of pneumonic plague, *Y. pestis* is considered a likely biological threat agent. At present, there is no effective licensed vaccine for plague, and diagnostic assays are limited. Thus, the need exists for the development of sensitive and specific diagnostic assays to detect plague infection, and effective vaccines for people living in or traveling to areas in which plague is endemic, for laboratory workers handling specimens from plague patients, and for high-risk individuals who may be exposed to aerosolized *Y. pestis* in a bioterrorist attack.

The two main protective antigens of *Yersinia pestis* are the Virulence (V) antigen and the F1 capsular antigen. The V-antigen is a protein that is required for virulence and is also a protective antigen against lethal infection by *Y. pestis* (T. W. Burrows, 1957, Virulence of *Pasteurelia pestis*, Nature, 179: 1246-1247; T. Une et al., 1984, J. Immunol. 133 (4): 2226-2230; R. D. Perry and J. D. Fetherston, 1997, Clin. Microbiol. Rev. 10: 35-66). Active immunization with V-antigen or V-antigen containing recombinant antigens confers a high level of protection to both parenteral and aerosol-induced mortality by homologous strains of *Y. pestis* in mice (S. E. C. Leary et al., 1995, Contr. Microbiol. Immunol. 13: 216-217; S. E. Leary et al., 1995, Infect. 1 mm. 63: 2854-2858; G. W. Anderson et al., 1996, Infect. Immun. 64: 4580-4585). Passive transfer of antibody-containing serum from V-immunized mice to naïve mice protected the naïve mice from a subsequent lethal parenteral or aerosol challenge with *Y. pestis* (T. Une et al., 1987, Microbiol. Immunol. 9: 179-185; V. L. Motin et al., 1994, Infect. 1 mm. 62: 4192-4201; A. Roggenkamp et al., 1997, Infect. 1 mm. 65: 446-451). A monoclonal antibody (mAb) specific for a peptide on the V antigen has been reported to passively protect mice against a challenge with a low infectious dose of *Y. pestis* given subcutaneously (J. Hill et al., 1997, Infect. 1 mm. 65: 4476-4482). Passive protection against a lethal aerosol challenge with *Y. pestis* in mice using anti-V monoclonal antibodies has not been previously demonstrated.

In order to identify potentially important epitopes on the V-antigen, monoclonal antibodies to a recombinant V antigen (rV) were generated. Hybridoma supernatants were screened for reactivity to *Y. pestis* rV by ELISA. A panel of 84 mAbs specific for the V antigen was generated and have been assigned to 38 binding groups. Four hybridomas were chosen for further study: 74-1, 84-1, 125-1, and 141-1. Surprisingly, the mAbs produced from these hybridomas, mAb 74-1, mAb 84-1, mAb 125-1, and mAb 141-1, were found to protect mice from a lethal aerosol dose of *Y. pestis* strain C12. This is the first time anti-V mAbs were shown to protect against an aerosol challenge. Previous experimental results suggest that it is significantly more difficult to protect against the capsule-negative, F1-negative C12 strain of *Y. pestis* as compared to the capsule-positive, F1-positive CO92 strain. The finding that mAbs with this specificity are protective is novel and unexpected. In general, it is usually easier to protect against a subcutaneous challenge than an aerosol one. Bubonic plague resulting from a subcutaneous infection or challenge usually involves the lymphatic system and takes more time to develop. Pneumonic plague which involves the respiratory system is harder to protect partly because of the delay in serum antibodies diffusing into the respiratory system where the bacteria resides. The second reason is that unlike the capsular antigen (F1) which is expressed on the surface of the bacteria, the V antigen is not believed to be abundantly expressed on the surface of the bacteria. The V antigen is usually released in the environment surrounding the bacteria. Therefore, one would expect that it would be easier to protect with anti-F1 antibodies which can readily bind to the surface bound F1 antigen and neutralize the pathogen.

SUMMARY OF THE INVENTION

Therefore, this application describes protective V-antigen-specific mAbs. The antibodies are classified into four binding groups. All the mAbs protect mice from a lethal aerosol dose of *Y. pestis* strain C12 when the mAbs are administered to mice prior to challenge. The mAbs of the present invention may be used as a prophylactic or therapeutic treatment for *Y. pestis* infections in other animal species, or in people. In addition, these mAbs are able to detect and capture V-antigen and can be incorporated into a specific, rapid diagnostic assay for the sensitive detection of V antigen of *Y. pestis*.

Therefore, it is an object of the present invention to provide monoclonal antibodies which protect against an aerosol challenge with *Y. pestis* and bind to epitopes on the *Y. pestis* V-antigen. Such antibodies are, for instance, produced by the hybridoma cell lines 74-1, deposit designation PTA-6289, 84-1, deposit designation PTA-6290, 125-1, deposit designation PTA-6291, and 141-1, deposit designation PTA-6292, deposited under the Budapest Treaty at American Type Culture Collection, Manassas, Va. on Nov. 9, 2004.

It is another object of the invention to provide for antibodies that are functionally equivalent to the antibodies listed above. These functionally equivalent antibodies substantially share at least one major functional property with an antibody listed above and herein described comprising: binding specificity to V antigen, protection against aerosol challenge when administered prophylactically or therapeutically, or competition for the same binding site on *Y. pestis* V antigen. The antibodies can be of any class such as IgG, IgM, or IgA or any subclass such as IgG1, IgG2a, and other subclasses known in the art. Further, the antibodies can be produced by any method, such as phage display, or produced in any organism or cell line, including bacteria, plant, insect, mammal or other type of cell or cell line which produces antibodies with desired characteristics, such as humanized antibodies. The antibodies can also be formed by combining an Fab portion and a Fc region from different species.

The monoclonal antibodies of the present invention described below recognize epitopes on *Y. pestis* V antigen. The immunogen was a recombinant V antigen obtained from Dr. P. Worsham of the Bacteriology Division of USAMRIID (Leary, S. et al., 1995, Infect. Imm. 63, 2854-2858).

The sequence of the V antigen is presented in SEQ ID NO:1. This sequence or portions thereof can be used as immunogens for the production of protective antibodies, polyclonal or monoclonal, which recognize V antigen of *Y. pestis*. The method for generating antibodies using peptides is well known in the art.

It is another object of the present invention to provide for mixtures of antibodies according to the present invention, as well as to methods of using individual antibodies, or mixtures thereof for the prevention and/or therapeutic treatment of *Y. pestis* infections in vitro and in vivo, and/or for improved detection of *Y. pestis* infections.

It is yet another object of the present invention to treat or prevent *Y. pestis* infection by administering a therapeutically or prophylactically effective amount of one antibody of the present invention or a mixture of antibodies of the present invention to a subject in need of such treatment.

It is another object of the present invention to provide passive vaccines for treating or preventing *Y. pestis* infections comprising a therapeutically or prophylactically effective amount of one or more the antibodies of the present invention which protect against *Y. pestis* disease, in combination with a pharmaceutically acceptable carrier or excipient.

It is still another object of the present invention to provide novel immunoprobes and test kits for detection of *Y. pestis*. For immunoprobes, the antibodies are directly or indirectly attached to a suitable reporter molecule, e.g., an enzyme or a radionuclide. The test kit includes a container holding one or more antibodies according to the present invention and instructions for using the antibodies for the purpose of binding to said V antigen of said *Y. pestis* to form an immunological complex and detecting the formation of the immunological complex such that presence or absence of the immunological complex correlates with presence or absence of said *Y. pestis* or *Y. pestis* antigens.

It is another object of the present invention to provide anti-idiotypic antibodies raised against one of the present monoclonal antibodies for use as a vaccine to elicit an active anti-V-antigen response.

It is yet another object of the present invention to provide antigenic epitopes as a component of a *Y. pestis* vaccine. The epitope of two of the monoclonal antibodies, mAb 141-1 and mAb 84-1 has been mapped to amino acids 161-176 of V-antigen (SEQ ID NO:2) and amino acids 4-18 of the V-antigen (SEQ ID NO:3), respectively. These epitopes of V-antigen, or conservative changes thereof which are still recognized by the antibodies, are useful for actively immunizing a host to elicit production of protective antibodies against *Y. pestis*.

BRIEF DESCRIPTION OF THE DRAWINGS

These and other features, aspects, and advantages of the present invention will become better understood with reference to the following description and appended claims, and accompanying drawings where:

DETAILED DESCRIPTION

In the description that follows, a number of terms used in recombinant DNA and immunology are extensively utilized. In order to provide a clearer and consistent understanding of the specification and claims, including the scope to be given such terms, the following definitions are provided.

The term "antibody" is art-recognized terminology and is intended to include molecules or active fragments of molecules that bind to known antigens. Examples of active fragments of molecules that bind to known antigens include Fab and $F(ab')_2$ fragments. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. *J. Nucl. Med.* 23:1011-1019 (1982). The term "antibody" also includes bispecific and chimeric antibodies.

The language "monoclonal antibody" is art-recognized terminology. The monoclonal antibodies of the present invention can be prepared using classical cloning and cell fusion techniques. The immunogen (antigen) of interest is typically administered (e.g. intraperitoneal injection) to wild type or inbred mice (e.g. BALB/c) or transgenic mice which produce desired antibodies, rats, rabbits or other animal species which can produce native or human antibodies. The immunogen can be administered alone, or mixed with adjuvant, or expressed from a vector (replicon vector, vaccinia), or as DNA, or as a fusion protein to induce an immune response. Fusion proteins comprise the peptide against which an immune response is desired coupled to carrier proteins, such as β-galactosidase, glutathione S-transferase, keyhole limpet hemocyanin (KLH), and bovine serum albumin, to name a few. In these cases, the peptides serve as haptens with the carrier proteins. After the animal is boosted, for example, two or more times, the spleen is removed and splenocytes are extracted and fused with myeloma cells using the well-known processes of Kohler and Milstein (Nature 256: 495-497 (1975)) and Harlow and Lane (*Antibodies: A Laboratory Manual* (Cold Spring Harbor Laboratory, New York 1988)). The resulting hybrid cells are then cloned in the conventional manner, e.g. using limiting dilution, and the resulting clones, which produce the desired monoclonal antibodies, cultured.

The term "epitope" is art-recognized. It is generally understood by those of skill in the art to refer to the region of an antigen or antigens that interacts with an antibody. An epitope of a peptide or protein antigen can be formed by contiguous or noncontinguous amino acid sequences of the antigen. The V antigen, like many proteins, contains many epitopes. The epitopes or peptides recognized by the antibodies of the present invention and conservative substitutions of these peptides which are still recognized by the antibody are an embodiment of the present invention. These peptides offer a convenient method for eluting V antigen to mAb 74-1, 84-1, 125-1, and 141-1 on immunoaffinity columns. For example, when an antibody which recognizes the epitope for mAb 84-1 is used in an immunoaffinity column to purify V antigen, the peptide recognized by the antibody can be added to the immunoaffinity column to elute the V antigen. Further truncation of these epitopes may be possible since antigenic epitopes have been reported to be represented by as few as five amino acid residues.

Epitope mapping studies described in this application show that mAb 141-1 recognizes an epitope on V antigen consisting of 11 amino acids (SEQ ID NO:2), and that mAb 84-1 recognizes a different epitope on V antigen consisting of 15 amino acids (SEQ ID NO:3). Antibodies which compete with mAb 141-1 or mAb 84-1 are considered to recognize the epitope of each respective antibody and are considered equivalent to the antibodies of the present invention. Assays for determining whether or not an antibody competes with an antibody of the present invention are known to a person with ordinary skill in the art and are described below.

By further mapping of the binding site of the monoclonal antibodies described in this application other peptides useful as a vaccine or a therapeutic can be predicted. Therefore, in another aspect, this invention relates to a method for identifying protective antigenic epitopes as described in the Examples below. Other methods are known in the art and include a method comprising (i) reacting a monoclonal antibody described in this application to different overlapping fragments encompassing the complete antigen, (ii) identifying a fragment to which the protective antibody binds, (iii) narrowing the region containing sites further by reacting the monoclonal with smaller overlapping fragments encompassing the region identified in (ii), and (iv) choosing peptides to which the antibody binds as possible antigenic epitopes. The peptides can then be assayed for their ability to protect an animal from disease, or to reduce the severity of disease. Peptides defining antigenic protective epitopes can be used in a vaccine as described below and in the Examples.

The epitopes or peptides to which the monoclonal antibodies of the present invention bind can constitute all or part of an eventual active vaccine candidate. An active vaccine or therapeutic candidate might comprise these peptide sequences and others. These might be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin can be added to increase antigen processing for more effective immune responses.

The present invention also pertains to hybridomas producing antibodies which bind to an epitope of V antigen. The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The present invention still further pertains to a method for detecting Y. pestis V antigen in a sample suspected of containing Y. pestis V antigen. The method includes contacting the sample with an antibody which binds an epitope of V antigen, allowing the antibody to bind to V antigen to form an immunological complex, detecting the formation of the immunological complex and correlating the presence or absence of the immunological complex with the presence or absence of V antigen in the sample. The sample can be biological, environmental or a food sample.

The language "detecting the formation of the immunological complex" is intended to include discovery of the presence or absence of V antigen in a sample. The presence or absence of V antigen can be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York 1988 555-612). Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a Y. pestis vaccinee and a monoclonal antibody of the present invention, are allowed to compete for binding of the antigen. The amount of monoclonal bound is then measured, and a determination is made as to whether the serum contains anti V antigen antibodies. This competitive ELISA can be used to indicate immunity to known protective epitopes in a vaccinee following vaccination and to identify competing antibodies.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 81:1-40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, biological fluid, or a solution for administering to a subject, such as a vaccine, or immunoglobulin. By "environmental sample" is meant a sample such as soil and water. Food samples include canned goods, meats, and others.

Yet another aspect of the present invention is a kit for detecting V antigen in a biological sample. The kit includes a container holding one or more antibodies which binds an epitope of V antigen and instructions for using the antibody for the purpose of binding to V antigen to form an immunological complex and detecting the formation of the immunological complex such that the presence or absence of the immunological complex correlates with presence or absence of V antigen in the sample. Examples of containers include multiwell plates which allow simultaneous detection of V antigen in multiple samples.

As described in greater detail in the Examples, the present inventors have isolated four monoclonal antibodies which bind to epitopes on V antigen and display in vitro and/or in vivo protective properties. Significantly, the reactivity of the mAbs is applicable against a broad variety of different wild type and laboratory *Y. pestis* strains of different types as determined in vitro using ELISA, western blot, radioimmunoprecipitation; or in vivo against challenge with *Y. pestis*. Wild type strains include for example Angola, Antiqua, Harbin 35, Pestoides A, Pestoids B, Pestoids C, Pestoides D, Pestoides Aa, Pestoides Ba, Pestoides F, Pestoides G, Pestoides J, CO92, KIM, Nicholisk 41, 195P, Indian isolate 111, EV76, Java 9, La Paz, Russian vaccine strain, Stavropol, 684, 538, 7752, Alexander, Dobson, Shasta, 242, A12, 564, 1171, South Park, and Yreka. Laboratory strains can be derived from wild type strains and include those which have been adapted, and those derived by site-directed mutagenesis such as various C092 derivatives including C092 Pgm-, C092 Lcr-, C092 pPst, C12, and others.

Given these results, monoclonal antibodies according to the present invention are suitable both as therapeutic and prophylactic agents for treating or preventing *Y. pestis* infection in susceptible plague-infected subjects. Subjects include rodents such as mice or guinea pigs, non-human primates, and other mammals, including humans.

In general, this will comprise administering a therapeutically or prophylactically effective amount of one or more monoclonal antibodies of the present invention to a susceptible subject or one exhibiting plague infection. Any active form of the antibody can be administered, including Fab and F(ab')$_2$ fragments. Antibodies of the present invention can be produced in any system, including insect cells, baculovirus expression systems, chickens, rabbits, goats, cows, or plants such as tomato, corn, potato, banana or strawberry. Antibodies of the present invention can also be humanized in order to mitigate potential side effects associated with injection of non-human materials. Methods for the production of antibodies in these systems are known to a person with ordinary skill in the art. Preferably, the antibodies used, especially humanized antibodies, are compatible with the recipient species such that the immune response to the mAbs does not result in clearance of the mAbs before bacteria can be controlled, and the induced immune response to the mAbs in the subject does not induce "serum sickness" in the subject. Preferably, the mAbs administered exhibit some secondary functions such as binding to Fc receptors of the subject.

Treatment of individuals having *Y. pestis* infection may comprise the administration of a therapeutically effective amount of one or more of the monoclonal antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to V antigen, or an antibody capable of protecting against plague in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg-100 pg/kg, 100 pg/kg-500 pg/kg, 500 pg/kg-1 ng/kg, 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg, 500 mg/kg-1 g/kg, 1 g/kg-5 g/kg, 5 g/kg-10 g/kg (body weight of recipient), although a lower or higher dosage may be administered.

In a similar approach, another therapeutic use of the monoclonal antibodies of the present invention is the active immunization of a patient using an anti-idiotypic antibody raised against one of the present monoclonal antibodies. Immunization with an anti-idiotype which mimics the structure of the epitope could elicit an active V antigen response (Linthicum, D. S. and Farid, N. R., Anti-Idiotypes, Receptors, and Molecular Mimicry (1988), pp 1-5 and 285-300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide, with or without adjuvant, in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof. Alternative protein modification techniques may be used e.g., $NH_2$-acetylation or COOH-terminal amidation, to provide additional means for coupling or fusing the peptide to another protein or peptide molecule or to a support.

The antibodies capable of protecting against *Y. pestis* are intended to be provided to recipient subjects in an amount sufficient to effect a reduction in the *Y. pestis* infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Controlled release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestible liquid or solid formulation.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 day, and 6 days (ii) 0, 7 days and 1 month, (iii) 0 and 1 month, (iv) 0 and 6 months, (v) 0, 1 month and 6 months, or other schedules sufficient to elicit the desired responses expected to reduce disease symptoms, or reduce severity of disease.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Recombinant Antigen and Bacteria

The recombinant V antigen (rV) was obtained from Dr. P. Worsham of the Bacteriology Division of USAMRIID. The virulent *Y. pestis* strains C092 pgm- and C12, an isogenic capsule-negative derivative of C092 were also provided by the Bacteriology Division, USAMRIID. The C12 mutant has 2 stop codons introduced by site-directed mutagenesis at the N-terminus of the structural gene that prevent F1 biosynthesis. Overnight cultures are maintained in fresh heart infusion broth.

Production of mAbs

BALB/C mice were injected intraperitoneally with 10 µg of rV antigen adsorbed in aluminum hydroxide. The mice received 2 additional booster injections 4 weeks and 8 weeks post-primary injection. One week after the last injection, the mice were bled and their sera tested for reactivity to rV antigen in a direct binding ELISA (see below). The mice with the highest ELISA reactivity were sacrificed and its spleen cells were fused as previously described (Stiles et al, Toxicon 29, 1195-1204, 1991). The resulting hybridoma culture supernatants were screened for reactivity to *Y. pestis* rV by ELISA as described below. Hybridoma whose culture supernatants reacted with rV were subcloned twice by limiting dilution to ensure clonality. Large-scale preparations of mAbs were done by culturing selected hybridoma cell lines in serum-free hybridoma culture medium in T150 Integra Cell-line Flasks. Purified mAbs were prepared by adsorption and elution from Protein G affinity columns. The concentrations of mAb preparations were determined by a BCA protein assay kit (Pierce), or by determining the OD at 280 nm.

Characterization of mAbs

Isotype Determination: Antibody classes and subclasses were determined by ELISA (BioRad). Briefly, 96-well microtiter plates were coated with 1.0 µg/well of rV antigen. Hybridoma culture supernatants are added to the wells in triplicate and allow to bind to the rV antigen coat. The isotype of the bound mAb is determined by the addition of isotype-specific secondary antibodies conjugated to alkaline phosphatase and the appropriate substrate.

Direct Binding ELISA: Specific reactivity of the mAbs with rV protein was determined by direct binding ELISA. Briefly, 96-well microtiter plates were coated with 0.1 µg/well of rV or with 0.1 µg/well recombinant F1 capsular antigen (rF1, negative control) and dried overnight. The dried wells were stored at −20° C. for use. The wells were blocked with PBS containing casein for 1 hr at 37° C., and washed 3× with PBS/TWEEN-20™. Culture supernatants (50 µl) were added to the wells in triplicate, and incubated for an additional hour at 37° C. The wells were washed and the appropriate dilution of goat anti-mouse γ-chain antibody conjugated to horseradish peroxidase (HRP, Sigma) was added and the wells incubated for 1 hr at 37° C. Reactivity was detected by the addition of the substrate, 2,2'-Azinobis-[3-ethylbenzothizoline-6-sulfonic acid] diammonium salt (ABTS) (Kirkegaard and Perry Laboratories, KPL).

In-Vivo Passive Transfer Experiments

To test for the ability of the mAbs to passively protect against a lethal aerosol challenge of *Y. pestis* strain C12, groups of 6 mice each were injected intraperitoneally with purified anti-V mAbs. They were challenged by whole-body (aerosol) exposure to 25 $LD_{50}$ of *Y. pestis* 18 hr post mAb administration. The numbers of surviving mice and the time to death are recorded for each group.

*Y. pestis* V Antigen Capture ELISA

For the detection assay, a predetermined concentration of rabbit anti-V antibodies were used to coat microtiter wells, which were dried overnight and stored at −20° C. for future use. After washing and blocking, various amounts of rV antigen were added to the wells and incubated for 1 hr at 37° C. The wells were then washed, and anti-V mAb conjugated to biotin are added. Binding of the antibodies to the rV was detected by addition of avidin conjugated to horseradish peroxidase (HRP) and the appropriate substrate.

For the capture assay, a similar ELISA was performed except that anti-V mAbs were used to coat microtiter plates. The coated anti-V mAbs will capture the added rV which was then detected with a rabbit anti-V antibody preparation.

Competitive Inhibition Enzyme-linked Immunosorbent Assay

Microtiter plates (Costar; Cat. # 3361) are coated with 50 μl/well of recombinant V (rV) at a concentration of 2.0 μg/ml in Ammonium Bicarbonate buffer (pH 8.8). The plates are allowed to dry for 48 hr at room temperature and stored at −20° C. for future use. Mixtures containing biotinylated anti-V antibody predetermined to provide approximately 50%-70% inhibition and known amounts of unconjugated anti-V antibody (inhibitor) diluted in Casein in Phosphate Buffer Saline (PBS, Pierce Cat # 37528) are added to the V-coated microtiter wells and allowed to incubate for 2 hr at 37° C. Similarly, mixtures containing biotinylated anti-V antibody and serial dilutions of unknown serum samples are added to the V-coated wells. After incubation, the wells are washed 3× with wash buffer (PBS with Tween 20, PBST). Conjugate Streptavidin Horseradish Peroxidase at a dilution of 1:8000 is then added and the wells incubated for 1 hr at 37° C. Following incubation, the wells are washed 3×, and ABTS Peroxidase Substrate (KPL, Cat # 50-62-00) is added. The optical density (OD) is determined at a wavelength of 410 nm. The percent inhibition is calculated based on the following formula: 100-[(OD in the presence of known amounts of anti-V antibodies of unknown serum samples×100)/(OD in the presence of normal serum)]. All assays are done in triplicates.

Mechanism of Action experiments

*Y. pestis* are treated with 5 ug/ml of anti-V antibodies and/or 5% rat C' for 1 hr, or left untreated. The treated bacteria are added to washed J774.A1 murine macrophages at a 10:1 ratio and the mixtures are incubated for 1 hr (Infection phase). After infection, the J774.A1 cells are washed, the macrophage cells are lysed, and the lysates are plated for colony count (t=0)—Opsonization. Similarly infected and washed J774.A1 macrophages are treated with gentamycin (7.5 ug/ml) for 1 hr to eliminate extracellular bacteria. Following incubation, the macrophages are washed and cultured either:

for an additional hr, lysed, and the lysate plated for colony count (t=2), or for an additional 17 hr, lysed, and the lysate plated for colony count (t=18)—Intracellular Killing.

Epitope Mapping

Our experimental approach to isolate and identify the V protective epitopes is based on the observation that peptide sequences bound to antibodies are protected from proteolytic (tryptic) digestion. Briefly, purified 141-1 or 84-1 anti-V mAb was covalently coupled to SEPHAROSE™ beads using CnBr overnight. The Antibody-beads complex was washed with at least three cycles of alternating pH buffers (1.5 ml of each of the following buffers: 0.1 M acetate buffer pH 4.0 containing 0.5 M NaCl followed by 0.1 M Tris-HCl buffer pH 8 containing 0.5 M NaCl). Recombinant V antigen in 0.1 M Ammonium Carbonate pH 8.0 was then added to the complex and incubated with mixing for 1 hr. The complex was then washed 3× with PBS pH 7.4 to get rid of unbound V Ag. Trypsin (500 pmole) was added and the proteolytic digestion was allowed to proceed overnight. Following digestion, the complex was washed 3× in PBS, pH 7.4. Elution of the bound V peptides after digestion was achieved by serially adding elution buffer (Pierce), incubating for 5 min, centrifuging and collecting the clear supernatant containing the protected peptides. This elution process was repeated 3-6×, or until one peptide was left bound to the antigen, yielding 3-6 eluted samples for biochemical analysis.

The eluted samples were subjected to liquid chromatography-sequential ion trap mass spectrometry (LC/MS/MS) with database search by Mascot to attempt to identify the peptide sequences. The results were mapped to amino acid sequence and crystal structure of the V antigen.

EXAMPLE 1

Generation and Specificity of anti-V Monoclonal Antibodies

Figure 1:
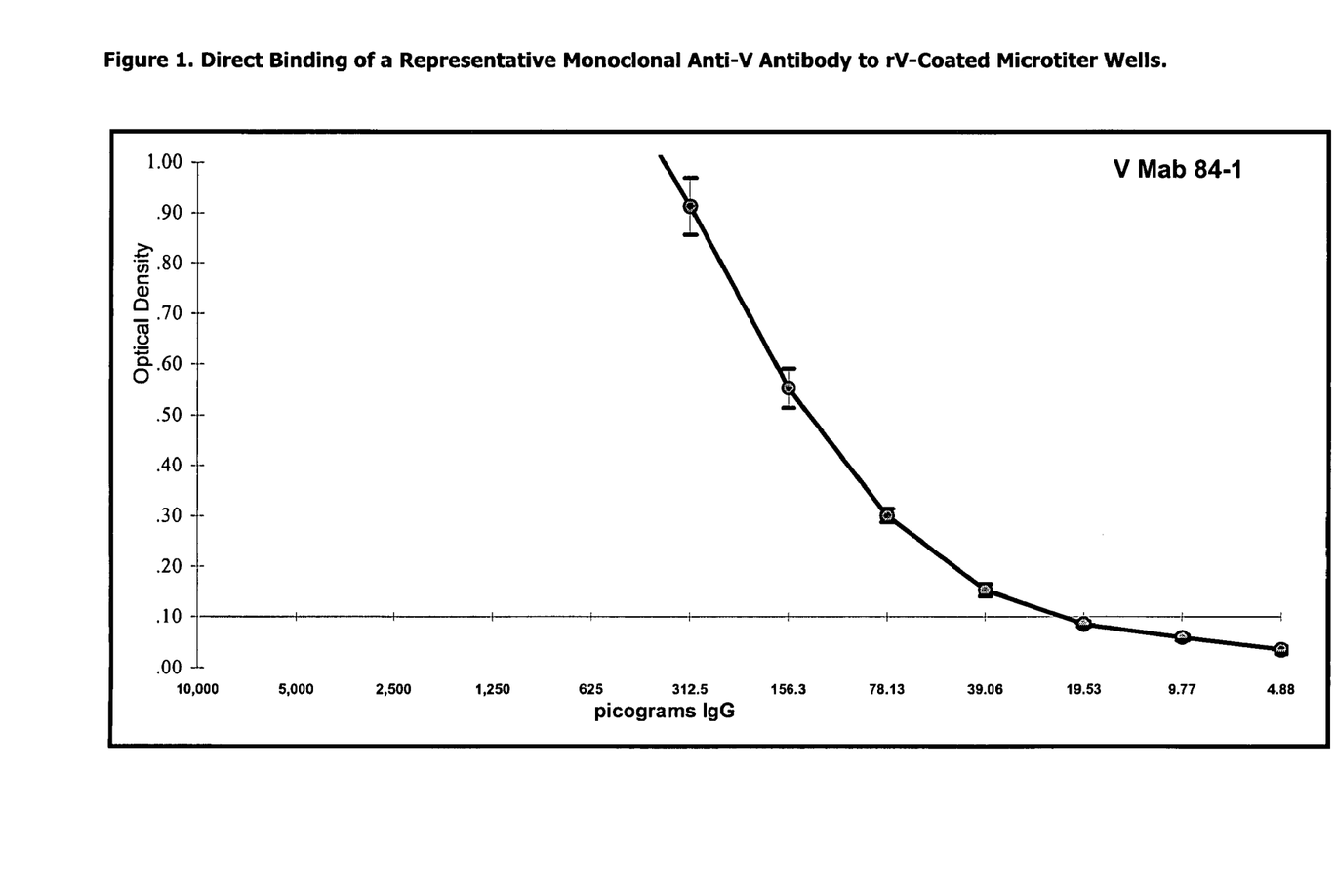
FIG. 1 Direct Binding of a Representative Monoclonal Anti-V Antibody to rV-Coated Microtiter Wells. X axis: amount of anti-V IgG (picograms). Y axis: optical density (OD).

A panel of 84 mAbs specific for the V antigen of *Y. pestis* has been generated. All are specific for V antigen as demonstrated by direct binding ELISA. The binding of a representative anti-V mAb (84-1) is shown in FIG. 1. 84-1 mAb bound well to rV with 78 picograms of antibody providing a binding with an optical density (OD) of approximately 0.3. None of the antibodies bound to the F1 capsular antigen of *Y. pestis*. Cross-inhibition assays have been conducted to determine their binding specificities. The 84 specific anti-V monoclonals have been assigned to thirty-eight binding groups and the cross reactivity among the binding groups has been determined. All of the binding groups show some overlapping reactivity with other binding groups. Twenty-one binding groups consist of individual clones. Twelve binding groups do not overlap with each other but do show cross reactivity with other binding groups. Four mAbs with the most promising characteristics were selected for further studies. They are designated mAb 74-1, mAb 84-1, mAb 125-1, and mAb 141-1.

EXAMPLE 2

Monoclonal Anti-V Antibodies Passively Protects Against A Lethal Aerosol Challenge with *Y. pestis*

Groups of six mice each were administered purified anti-V mAb intraperitoneally and challenged 18 hr thereafter with a lethal (25 $LD_{50}$) aerosol dose of *Y. pestis* strain C12. Table 1 shows the 4 selected anti-V mAbs and their respective ability to protect against an aerosol challenge of *Y. pestis*. In this particular experiment, 74-1 mAb provided the best protection; 4 mice survived out of 6 mice challenged. Other anti-V mAbs protected to a lesser extent. Although not all challenged mice survived, the results are significant and promising as this represents the first time anti-V mAbs were shown to protect against an aerosol challenge. Moreover, previous experimental results suggest that it is significantly more difficult to protect against the F1-negative C12 strain of *Y. pestis* (used in these experiment) as compared to the F1-positive CO92 strain (unpublished observations). Continuing experimentation is being conducted to titrate mAbs and challenge dosages, including *Y. pestis* strain CO92, and to determine the anti-V mAbs' prophylactic and therapeutic potentials.

EXAMPLE 3

Antigen Detection and Capture ELISA for the *Y. pestis* V Antigen

Among the 4 selected anti-V mAbs, all except antibody 74-1 were capable of both detecting and capturing rV antigen (Table 2). Monoclonal antibody 84-1 appears to be the best detecting and capturing antibody of the group. This demonstrates that the developed anti-V mAbs can be incorporated into specific, rapid diagnostic systems for the detection of small amounts of V antigen of *Y. pestis*.

TABLE 1

In Vivo Passive Transfer Protection Against Pneumonic Plague by Anti-V Monoclonal Antibodies

| Mouse No. | Anti-V mAbs | 1 | 2 | 3 | 4 | 5 | 6 | 7 | 8 | 9 | 10 | 11 | 12 | 13 | 14 | 15 | Survivors/Total |
|---|---|---|---|---|---|---|---|---|---|---|---|---|---|---|---|---|---|
| 1 | 141-1 |   |   | D[a] | — | — | — | — | — | — | — | — | — | — | — | — | 3/6 |
| 2 |       |   |   |   | D | — | — | — | — | — | — | — | — | — | — | — |     |
| 3 |       |   |   |   |   |   |   | D | — | — | — | — | — | — | — | — |     |
| 4 |       |   |   |   |   |   |   |   |   |   |   |   |   |   |   | S[b] |   |
| 5 |       |   |   |   |   |   |   |   |   |   |   |   |   |   |   | S |     |
| 6 |       |   |   |   |   |   |   |   |   |   |   |   |   |   |   | S |     |
| 1 | 125-1 |   |   |   |   |   |   | D | — | — | — | — | — | — | — | — | 3/6 |
| 2 |       |   |   |   |   |   |   | D | — | — | — | — | — | — | — | — |     |
| 3 |       |   |   |   |   |   |   |   |   | D | — | — | — | — | — |     |
| 4 |       |   |   |   |   |   |   |   |   |   |   |   |   |   |   | S |     |
| 5 |       |   |   |   |   |   |   |   |   |   |   |   |   |   |   | S |     |
| 6 |       |   |   |   |   |   |   |   |   |   |   |   |   |   |   | S |     |
| 1 | 84-1  |   |   |   |   |   | D | — | — | — | — | — | — | — | — | — | 3/6 |
| 2 |       |   |   |   |   |   | D | — | — | — | — | — | — | — | — | — |     |
| 3 |       |   |   |   |   |   |   | D | — | — | — | — | — | — | — |     |
| 4 |       |   |   |   |   |   |   |   |   |   |   |   |   |   |   | S |     |
| 5 |       |   |   |   |   |   |   |   |   |   |   |   |   |   |   | S |     |
| 6 |       |   |   |   |   |   |   |   |   |   |   |   |   |   |   | S |     |
| 1 | 74-1  |   |   |   |   |   | D | — | — | — | — | — | — | — | — | — | 4/6 |
| 2 |       |   |   |   |   |   | D | — | — | — | — | — | — | — | — | — |     |
| 3 |       |   |   |   |   |   |   |   |   |   |   |   |   |   |   | S |     |
| 4 |       |   |   |   |   |   |   |   |   |   |   |   |   |   |   | S |     |
| 5 |       |   |   |   |   |   |   |   |   |   |   |   |   |   |   | S |     |
| 6 |       |   |   |   |   |   |   |   |   |   |   |   |   |   |   | S |     |
| 1 | Neg. Ctrl. |   |   |   | D | — | — | — | — | — | — | — | — | — | — | — | 0/6 |
| 2 |       |   |   |   | D | — | — | — | — | — | — | — | — | — | — | — |     |
| 3 |       |   |   | D | — | — | — | — | — | — | — | — | — | — | — | — |     |
| 4 |       |   |   | D | — | — | — | — | — | — | — | — | — | — | — | — |     |
| 5 |       |   |   |   |   |   | D | — | — | — | — | — | — | — | — | — |     |
| 6 |       |   |   |   |   |   | D | — | — | — | — | — | — | — | — | — |     |

[a]Dead;
[b]Survived

TABLE 2

Summary of *Y. pestis* V Monoclonal Antibodies Used in Immunodiagnostic Assays

| Mab ID | Detector | O.D.[a] (avg.) | Capture | 1000[b] | 4000 | 16000 | 64000 | Titer | Sum[c] |
|---|---|---|---|---|---|---|---|---|---|
| 74.1  | Yes | 2.06 | No  | 0.08 | 0.11 | −0.01 | −0.03 | Neg   | 0.15 |
| 10-1  | Yes | 2.75 | Yes | 0.21 | 0.04 | 0.01  | −0.09 | 1000  | 0.17 |
| 84-1  | Yes | 2.71 | Yes | 1.58 | 2.23 | 1.33  | 0.21  | 16000 | 5.35 |
| 124.1 | Yes | 2.07 | Yes | 0.92 | 0.69 | 0.85  | 0.19  | 16000 | 2.65 |
| 141.1 | Yes | 1.39 | Yes | 0.93 | 1.35 | 0.55  | 0.01  | 16000 | 2.84 |

"Sum" refers to the approximate area under the curve.
[a]Optical Density
[b]Reciprocal dilution of culture supernatant tested
[c]Sum of all O.D.

EXAMPLE 4

Competitive Inhibition Enzyme-Linked Immunosorbent Assay (ELISA)

Figure 2A:
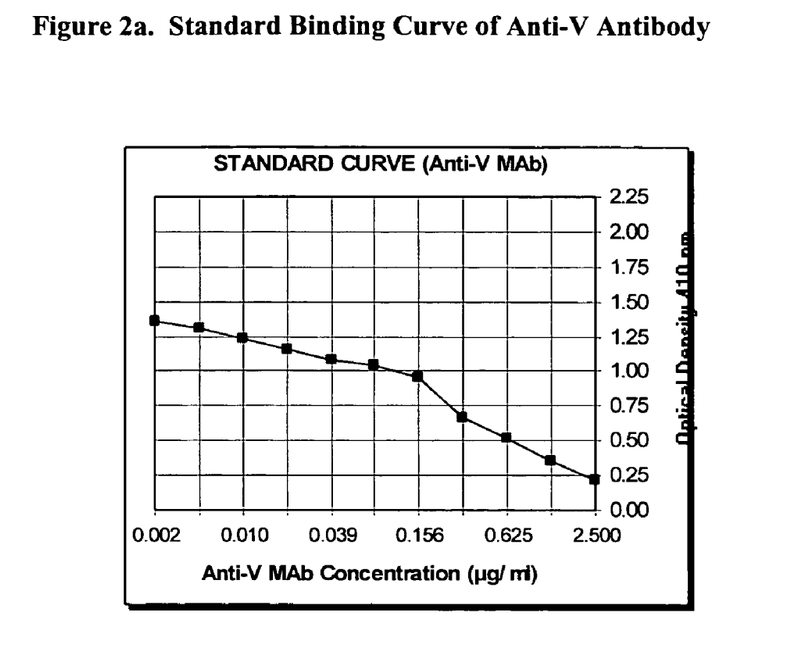
FIGS. 2A and 2B-A, Standard Binding Curve of Anti-V Antibody. X axis: concentrations of anti-V antibody (μg/ml). Y axis: OD. B. Standard Inhibition Curve of Anti-V Antibody. X axis: concentrations of anti-V antibodies (μg/ml), Y axis: percent (%) inhibition of binding.
Figure 2B:
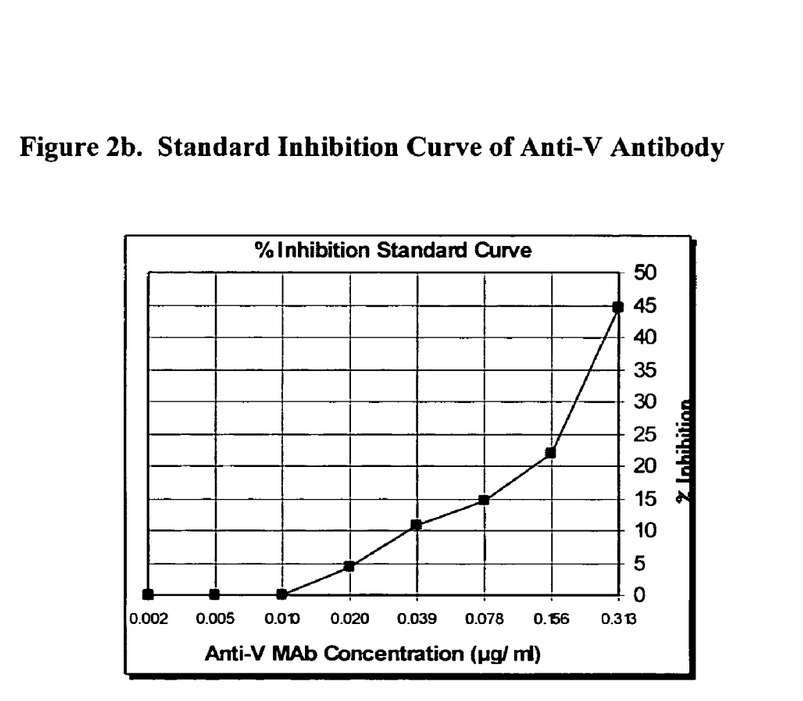

FIGS. 2a and 2b show the standard binding curve and the standard inhibition curve, respectively, obtained using the CIE described above. As known concentrations of anti-V antibodies added increase from 0.002 µg/ml to 2.5 µg/ml, the binding of the biotinylated anti-V antibody to V-coated wells concomitantly decreases from an OD of ~1.35 to an OD of −0.24 (FIG. 2a). When the OD of binding are converted to percent inhibition of binding based on the formula given above, one obtains a standard inhibition curve shown in FIG. 2b. Thus, anti-V antibody at a concentration of 0.313 µg/ml provides ~45% inhibition of binding. As the concentration of known amounts of antibody decreases, a concomitant decrease in the percent inhibition is observed. The CIE is highly sensitivity, capable of detecting as little as 0.02 µg/ml or 20 ng/ml of anti-V antibodies (% inhibition of −5%). The percentages of inhibition of binding obtained with unknown serum samples are simply plotted on this standard inhibition curve for the determination of the amounts of anti-V antibodies in the unknown samples. This CIE assay is developed to attempt to positively correlate the amounts of anti-V antibodies in the serum at the time of challenge with survival from challenge.

EXAMPLE 5

Potential Mechanism of Anti-V Antibody-Mediated Protection

We have demonstrated that anti-V antibodies are capable of protecting mice against a lethal aerosol challenge with *Y.*

*pestis* by passively transferring the anti-V antibodies prior to challenge. To elucidate the mechanism of this antibody-mediated protection, untreated or anti-V and Complement (C) treated *Y. pestis* are used to infect a murine macrophage cell lines (J774.A1) as described in Materials and Methods.

The results of a representative experiment are shown in Table 3. Untreated or anti-V antibody and Complement (C, 5%) treated *Y. pestis* were used to infect murine macrophages J774.A1. After 1 hr of infection, the macrophages were washed and lysed. The lysates were plated on blood agar plates for colony count to enumerate intracellular bacteria (t=0, Table 3). When *Y. pestis* were treated with PBS, 5.8% of the original inoculum was found inside the macrophages at T=0. Treatment with Anti-V and C resulted in an increase in the number of bacteria taken up by the macrophages, especially at 5.0 µg/ml and 10 µg/ml of anti-V antibody. Most significantly, after 18 hr of incubation, the number of bacteria in macrophages infected with PBS-treated *Y. pestis* slightly increased (104.60% of the number of bacteria in the macrophages at T=0). On the other hand, the number of bacteria in macrophages infected with bacteria treated with anti-V antibody and C decreased dramatically. Only 15.88% (1.0 ug/ml anti-V), 12.76% (5.0 ug/ml anti-V) and 2.21% (10 ug/ml anti-V) of the bacteria originally taken up by the macrophages were viable after 18 hr incubation (T=18). These results suggest two important mechanisms of protection mediated by the anti-V antibody. First, there was an enhanced uptake of anti-V-treated bacteria, a mechanism previously described as opsonization which helps clear the bacteria from circulation. Second, untreated bacteria were able to grow or at least remain unchanged numerically. However, treatment with anti-V antibody resulted in a concentration-dependent enhanced killing of intracellular bacteria such that only 2% to 15% of the bacteria originally taken up by the macrophages were viable after 18 hr of culture (T=18).

basis for the development of the next generation plague vaccine.

Using the methods previously described under Epitope Mapping section and taking advantage of the observation that antigenic peptides are protected from trypsin proteolysis by virtue of their prior binding to antibodies, we have used the 141-1 and 84-1 anti-V mAb to protect the V peptides that are bound by the mAb. After proteolysis and extensive washing to remove unbound peptides, we eluted fractions using a low pH eluting buffer.

Figure 3:
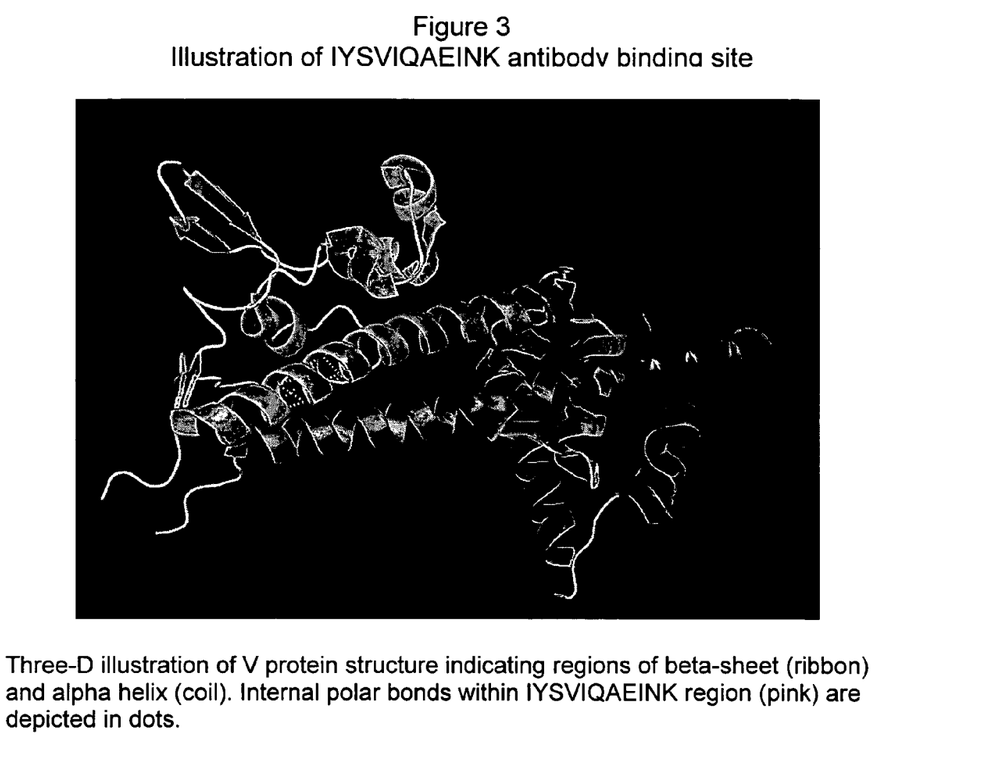
FIG. 3 Illustration of IYSVIQAEINK (SEQ ID NO:2) antibody binding site. Three-D illustration of V protein structure indicating regions of beta-sheet (ribbon) and alpha helix (coil). Internal polar bonds within IYSVIQAEINK (SEQ ID NO:2) region (pink) are depicted in dots.

The analysis of mAb 141-1 resulted in 3 eluted samples as follows. The experimental samples clearly contained peptides of amino acid sequences matching V protein sequence. The number of peptides diminished with the number of elution washes; 9 peptides in the $1^{st}$ fraction, 3 in the $2^{nd}$ fraction, and 1 in the $3^{rd}$ fraction. Since these samples represent serial elution, the degree of binding affinity (i.e. strength of binding) and specificity increase with the number of elutions. Thus, we have identified at least one V peptide sequence that is bound strongly and specifically to the 141-1 anti-V mAb (IYSVIQAEINK, SEQ ID NO:2). When this V peptide sequence is aligned on the whole V sequence and compared with previously published mildly protective sequences (aa 2-135 and 135-245), the identified V peptide (aa 161-176) in this study is located almost right in the middle of the V sequence Table 4. Peptide IYSVIQAEINK (SEQ ID NO:2) maps on the V protein 3-D structure, at the C-terminal end of central alpha-helix 5 where it juxtaposes helix 10 and near a flexible, undefined region of the protein (FIG. 3).

The results strongly suggest that we have identified a V peptide composed of 11 amino acids (IYSVIQAEINK, SEQ ID NO:2, with a molecular mass of 1276) which is bound tightly and specifically to the protective 141-1 anti-V mAb. This sequence is located within previously published sequences and further defines a significantly shorter peptide that may be able to induce protective immunity against aerosolized plague.

TABLE 3

Enhanced Uptake and Increased Intracellular Killing of Anti-V-Ab and C-Treated *Y. pestis*

| | | *Y. Pestis* Treated With | | | | | | |
|---|---|---|---|---|---|---|---|---|
| PBS | | Anti-V Ab (1.0 ug/ml) + 5% Complement | | Anti-V Ab (5.0 ug/ml) + 5% Complement | | Anti-V Ab (10.0 ug/ml) 5% Complement | | |
| T = 0 | T = 18 | T = 0 | T = 18 | T = 0 | T = 18 | T = 0 | T = 18 |
| $8.7 \times 10^4$ | $9.1 \times 10^4$ | $4.6 \times 10^4$ | $5.4 \times 10^3$ | $2.2 \times 10^5$ | $3.7 \times 10^3$ | $1.4 \times 10^5$ | $3.1 \times 10^3$ |
| $5.80^a$ | $104.60^b$ | $2.88^a$ | $15.88^b$ | $12.94^a$ | $12.76^b$ | $11.67^a$ | $2.21^b$ |

$^a$Percent of infecting inoculum, or percent uptake
$^b$Percent of phagocytosed bacteria at T = 0

EXAMPLE 6

We have demonstrated that the anti-V monoclonal antibodies (mAbs) in this disclosure protect against a lethal aerosol challenge of *Y. pestis* in a mouse animal model of pneumonic plague. Because of the protective nature of the mAbs, it can be presumed that the V peptides within the V antigen recognized by the mAbs represent protective epitopes, i.e. they are capable of inducing protective immunity against plague. The identification of these protective V epitopes may form the For mAb 84-1, six serial elutions were done. As with mAb 141-1, peptides bound in the first eluate include non-specific, low affinity as well as high affinity binding peptides. As we progressed to the $5^{th}$ eluate, only a single peptide remained. This is the peptide that is specifically and strongly bound to mAb 84-1. No peptide was found in the $6^{th}$ eluate. Therefore, we have identified the V-antigen epitope to which mAb 84-1 binds specifically. This peptide, AYEQNPQHFIEDLEK, is located at amino acids 4-18 of V antigen and is described in SEQ ID NO:3.

TABLE 4

Comparison of Protective V Epitopes Results To Prior Findings

```
  1 MIRAYEQNPQ HFIEDLEKVR VEQLTGHGSS VLEELVQLVK DKNIDISIKY

51 DPRKDSEVFA NRVITDDIEL LKKILAYFPL EDAILKGGHY DNQLQNGIKR

101 VKEFLESSPN TQWELRAFMA VMHFSLTADR IDDDILKVIV DSMNHHGDAR

151 SKLREELAEL TAELKIYSVI QAEINKHLSS SGTINIHDKS INLMDKNLYG

201 YTDEEIFKAS AEYKILERMP QTTIQVDGSE KKIVSIKDFL GSENKRTGAL

251 GNLKNSYSYN KDNNELSHFA TTCSDKSRPL NDLVSQKTTQ LSDITSRFNS

301 AIEALNRFIQ KYDSVMQRLL DDTSGK (SEQ ID NO: 1)
```

Sequences in italics and bold indicate sequences previously demonstrated to contain mildly protective domains of the V protein (Hill et al. 1997) including, the N-terminal region of amino acid 2-135; central region spanning amino acids 135-245.

Italics, bold and single-underline segment represents the tightest binding tryptic peptide observed for mAb 141-1: IYSVIQAEINK, SEQ ID NO:2, amino acids 161-176, of mass 1276.

Italics, bold with dashed-underline segment represents the tightest binding tryptic peptide observed for mAb 84-1: AYEQNPQHFIEDLEK, SEQ ID NO:2, amino acids 4-18.

What is claimed is:

1. An isolated monoclonal antibody specific for V-antigen of *Yersinia pestis* wherein said antibody passively protects mice from a lethal aerosol challenge with *Y. pestis* C12 strain when administered 18 hours prior to challenge.

2. The antibody according to claim 1, wherein said antibody is produced by any of hybridoma cell lines selected from the group consisting of 74-1, ATCC deposit PTA6289, 84-1, ATCC deposit PTA-6290, 125-1, ATCC deposit PTA 6291 and 141-1, ATCC deposit PTA-6292.

3. The antibody according to claim 1, wherein the antibody binds *Y. pestis* in vitro.

4. The antibody according to claim 3 wherein said antibody is selected from the group consisting of:
   an antibody produced by hybridoma 74-1, ATCC deposit PTA6289,
   an antibody produced by hybridoma 84-1, ATCC deposit PTA-6290,
   an antibody produced by hybridoma 125-1, ATCC deposit PTA 6291; and
   an antibody produced by hybridoma 141-1, ATCC deposit PTA-6292.

5. The antibody according to claim 1, wherein the antibody immunoprecipitates V antigen from supernatants or cell lysates of cell cultures infected with *Y. pestis*.

6. The antibody according to claim 5 wherein said antibody is selected from the group consisting of:
   an antibody produced by hybridoma 74-1, ATCC deposit PTA6289,
   an antibody produced by hybridoma 84-1, ATCC deposit PTA-6290,
   an antibody produced by hybridoma 125-1, ATCC deposit PTA 6291; and
   an antibody produced by hybridoma 141-1, ATCC deposit PTA-6292.

7. A composition comprising one or more isolated antibodies selected from the group consisting of:
   an antibody produced by hybridoma 74-1, ATCC deposit PTA6289,
   an antibody produced by hybridoma 84-1, ATCC deposit PTA-6290,
   an antibody produced by hybridoma 125-1, ATCC deposit PTA 6291; and
   an antibody produced by hybridoma 141-1, ATCC deposit PTA-6292.

8. An isolated hybridoma selected from the group consisting of: 74-1, ATCC deposit PTA6289, 84-1, ATCC deposit PTA-6290, 125-1, ATCC deposit PTA 6291 and 141-1, ATCC deposit PTA-6292.

9. A method of detecting, in a sample suspected of containing *Y. pestis*, said method comprising:
   (i) incubating the sample with an effective amount of at least one monoclonal antibody according to claim 2, under conditions which allow the formation of antibody-*Y. pestis* complex and
   (ii) detecting the complex wherein the presence or the absence of the complex indicates the presence or the absence of said *Y. pestis* in the sample.

10. The method according to claim 9, wherein said sample is a biological sample.

* * * * *